(12) United States Patent
Sarunic et al.

(10) Patent No.: US 7,903,256 B2
(45) Date of Patent: Mar. 8, 2011

(54) METHODS, SYSTEMS, AND COMPUTER PROGRAM PRODUCTS FOR PERFORMING REAL-TIME QUADRATURE PROJECTION BASED FOURIER DOMAIN OPTICAL COHERENCE TOMOGRAPHY

(75) Inventors: Marinko V. Sarunic, Durham, NC (US); Brian E. Applegate, Durham, NC (US); Joseph A. Izatt, Raleigh, NC (US)

(73) Assignee: Duke University, Durham, NC (US)

( * ) Notice: Subject to any disclaimer, the term of this patent is extended or adjusted under 35 U.S.C. 154(b) by 67 days.

(21) Appl. No.: 11/725,167

(22) Filed: Mar. 16, 2007

(65) Prior Publication Data
US 2008/0170219 A1 Jul. 17, 2008

Related U.S. Application Data

(60) Provisional application No. 60/782,915, filed on Mar. 16, 2006.

(51) Int. Cl.
*G01B 11/02* (2006.01)
(52) U.S. Cl. ........................................ 356/497
(58) Field of Classification Search .................. 356/479, 356/497
See application file for complete search history.

(56) References Cited

U.S. PATENT DOCUMENTS

| | | | |
|---|---|---|---|
| 5,313,266 A | 5/1994 | Keolian et al. | |
| 5,631,969 A | 5/1997 | Hanson | |
| 7,019,838 B2 * | 3/2006 | Izatt et al. | 356/479 |
| 2004/0239938 A1 | 12/2004 | Izatt | |
| 2004/0239943 A1 | 12/2004 | Izatt et al. | |
| 2004/0239946 A1 | 12/2004 | Kane et al. | |
| 2005/0280828 A1 | 12/2005 | De Boer | |
| 2006/0290939 A1 * | 12/2006 | Vakhtin et al. | 356/456 |
| 2008/0198367 A1 * | 8/2008 | Chang et al. | 356/73 |

FOREIGN PATENT DOCUMENTS

| WO | WO2007109127 | 9/2007 |
|---|---|---|
| WO | 2002201 | 12/2008 |

OTHER PUBLICATIONS

International Search Report and Written Opinion dated Feb. 14, 2008.

(Continued)

*Primary Examiner* — Tarifur Chowdhury
*Assistant Examiner* — Jonathon D Cook
(74) *Attorney, Agent, or Firm* — Jenkins, Wilson, Taylor & Hunt, P.A.

(57) ABSTRACT

Methods, systems, and computer program products for performing real-time quadrature projection based FDOCT are disclosed. According to one method, a plurality of interferogram signals is phase shifted. A Fourier transform is applied to each of the plurality of interferogram signals. Depth dependence of the plurality of transformed interferogram signals is then removed. A real quadrature component and an imaginary quadrature component for each of the plurality of transformed interferogram signals are subsequently calculated. The real quadrature components of the transformed interferogram signals are combined to obtain a derived real component and the imaginary quadrature components of the transformed interferogram signals are combined to obtain a derived imaginary component. A full-range depth profile of the object is constructed by adding the derived real component to the product of the derived imaginary component and a scaling factor. A full-range depth image of the object is then generated using the full-range depth profile.

39 Claims, 8 Drawing Sheets

OTHER PUBLICATIONS

Notice of Publication from European Patent Office dated Oct. 31, 2008.

Davis, A.M. et al, "Heterodyne Swept-Source Optical Coherence Tomography for Complete Complex Conjugate Ambiguity Removal," *J.Biomed. Optics*, vol. 10, No. 6, pp. 064005-1 to 064005-6, Nov./Dec. 2005.

Dorrer, Christophe et al., "Spectral Resolution And Sampling Issues In Fourier-Transform Spectral Interferometry," *J. Opt. Soc. Am. B*, vol. 17, No. 10, Oct. 2000, pp. 1795-1802.

Fercher, A.F. et al., "Measurement of Intraocular Distances by Backscattering Spectral Interferometry," *Optics Communications*, 117 (1995) pp. 43-48.

Götzinger, Erich et al., "High Speed Full Range Complex Spectral Domain Optical Coherence Tomography," *Optics Express*, Jan. 24, 2005 / vol. 13, No. 2 / 583.

Huang, David et al., "Optical Coherence Tomography," *Science, New Series*, vol. 254, No. 5035 (Nov. 22, 1991), pp. 1178-1181.

R. Huber, et al., "Amplified, frequency swept lasers for frequency domain reflectometry and OCT imaging: design and scaling principles," May 2, 2005 / vol. 13, No. 9 / *Optics Express* 3513.

Sarunic, Marinko V. et al., "Instantaneous Complex Conjugate Resolved Spectral Domain and Swept-Source OCT Using 3x3 Fiber Couplers," 7 Feb. 2005 / vol. 13, No. 3 / *Optics Express* 957.

Targowski, Piotr et al., "Improved Complex Spectral Domain OCT for In Vivo Eye Imaging," *Optics Communications* 249 (2005) 357-362.

Vakoc, B. J. et al., "Elimination of Depth Degeneracy in Optical Frequency-Domain Imaging Through Polarizationbased Optical Demodulation," *Optics Letters* / vol. 31, No. 3 / Feb. 1, 2006.

Wojtkowski, M. et al., "Full Range Complex Spectral Optical Coherence Tomography Technique in Eye Imaging," Aug. 15, 2002 / vol. 27, No. 16 / *Optics Letters* 1415.

Yun, S. H. et al, "Removing the Depth-Degeneracy in Optical Frequency Domain Imaging With Frequency Shifting," Oct. 4, 2004 / vol. 12, No. 20 / *Optics Express* 4822.

Zhang, Jun et al., "Removal of A Mirror Image and Enhancement of the Signal-To-Noise Ratio in Fourier-Domain Optical Coherence Tomography Using an Electro-Optic Phase Modulator," Jan. 15, 2005 / vol. 30, No. 2 / *Optics Letters* 147.

\* cited by examiner

METHODS, SYSTEMS, AND COMPUTER PROGRAM PRODUCTS FOR PERFORMING REAL-TIME QUADRATURE PROJECTION BASED FOURIER DOMAIN OPTICAL COHERENCE TOMOGRAPHY

CROSS-REFERENCE TO RELATED APPLICATIONS

This application claims the benefit of U.S. Provisional Patent Application Ser. No. 60/782,915, filed on Mar. 16, 2006. The content of this provisional application is incorporated herein by reference in its entirety.

GOVERNMENT RIGHTS

The present subject matter was made with United States Government support under Federal Grant No. EY013516 awarded by National Eye Institute (NEI). The United States Government may have certain rights to this invention.

TECHNICAL FIELD

The subject matter described herein relates to the utilization of Fourier domain (FD) transforms and their application to the fields of interferometry and optical coherence tomography (OCT). More particularly, the subject matter described herein relates to performing real-time, quadrature projection based FDOCT.

BACKGROUND

The development of optical coherence tomography (OCT) in recent years has concentrated on Fourier domain (FD) techniques for high speed cross-sectional imaging of biological tissue. Namely, FD techniques provide increased signal-to-noise ratio (SNR) and increased robustness over traditional OCT techniques. The SNR advantage of FDOCT techniques may be employed for faster image acquisition, thereby enabling practical three-dimensional OCT imaging in living subjects. In FDOCT, the locations of scatterers within a sample are obtained by Fourier transformation of real-valued spectral interferograms, which are generated by mixing light backscattered from the sample with reference light. The Fourier transform of the interferogram is Hermititan symmetric, thereby introducing a complex conjugate artifact in which positive and negative distances are not resolved. In practice, this symmetric artifact may be avoided by locating the sample entirely within the positive or negative displacement range, thus utilizing only one half of the potential total imaging depth. Such one sided imaging is suitable for thin objects, but imaging of extended objects is limited by the characteristic roll-off in sensitivity that is typically associated with the finite spectral resolution of FDOCT systems.

Full-range imaging, in which positive and negative distances are resolved, can be achieved by indirectly measuring the complex component of the interferometric OCT signal using techniques borrowed from phase shift interferometry. The imaginary component of the interferogram is obtained by shifting the phase of the reference reflection in increments of 90 degrees. Phase shifting has been demonstrated in spectrometer-based FDOCT systems using a discretely stepped piezoelectric transducer (PZT) mounted reflector or an electro-optic modulator in the reference arm. One drawback of sequentially shifting the interferogram is that significant image corruption results from small deviations (e.g., chromatic deviations) in the actual phase shift obtained or from small (i.e., sub-wavelength) sample motion between the phase shifted acquisitions.

Recently, the instantaneous acquisition of two phase shifted signals was demonstrated using linearly polarized light. This technique was limited by having only two phase shifted signals (which limits complex signal reconstruction) as well as by potential image corruption present in birefringent samples. Methods to instantaneously acquire three phase-shifted interferograms using 3×3 fused fiber couplers for both spectrometer-based and swept source (SS) FDOCT systems have also been employed. However, the performance of these types of systems for complex conjugate image reconstruction may be limited by the wavelength dependence of the splitting ratios associated with the fiber couplers. In addition, an approach to full range imaging based on frequency shifting may be considered, but this method would not compatible with spectrometer based systems.

Notably, all of the aforementioned phase shifting FDOCT techniques suffer image corruption arising from the miscalibration of the phase shifts as well as from the wavelength dependence of the phase shifter. Numerical techniques to improve the suppression of symmetric artifact by compensating for the phase shift irregularities and for by accounting for axial sample motion in between phase shifted acquisitions have been previously been presented. However, there have not been any methods that address the removal of the complex conjugate artifact present in FDOCT images.

Accordingly, there exists a need for an effective method for eliminating the complex conjugate artifact in FDOCT images.

SUMMARY

The subject matter described herein includes methods, systems, and computer program products for performing real-time quadrature projection based FDOCT. One method includes phase shifting a plurality of interferogram signals. A Fourier transform is applied to each of the plurality of interferogram signals. Depth dependence of the plurality of transformed interferogram signals is then removed. A real quadrature component and an imaginary quadrature component for each of the plurality of transformed interferogram signals are subsequently calculated. The real quadrature components of the transformed interferogram signals are combined to obtain a derived real component and the imaginary quadrature components of the transformed interferogram signals are combined to obtain a derived imaginary component. A full-range depth profile of the object is constructed by adding the derived real component to the product of the derived imaginary component and a scaling factor. A full-range depth image of the object is then generated using the full-range depth profile.

The subject matter described herein for performing real-time quadrature projection based FDOCT may be implemented in hardware, software, firmware, or any combination thereof. As such, the terms "function" or "module" as used herein refer to hardware, software, and/or firmware for implementing the feature being described. In one exemplary implementation, the subject matter described herein may be implemented using a computer program product comprising computer executable instructions embodied in a computer readable medium. Exemplary computer readable media suitable for implementing the subject matter described herein include disk memory devices, chip memory devices, programmable logic devices, application specific integrated circuits, and downloadable electrical signals. In addition, a computer program product that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings of which.

DETAILED DESCRIPTION

The present subject matter relates to a method for removing complex conjugate artifacts in FDOCT images by projecting phase shifted signals onto an orthogonal basis set using Fourier decomposition. In one embodiment quadrature projection processing is utilized. Quadrature projection involves the representation of phase shifted signals as vectors. The vectors are typically derived from the real and imaginary components of a phase shifted signal that has been subjected to a Fourier transform. These vectors are then projected onto the real and imaginary axes. One important aspect pertaining to quadrature projection processing is that it is insensitive to the miscalibrated phase shifts in 90 degree-shift interferometry and only requires predetermination of the quadrant location for each phase shift in non-90 degree phase shift techniques.

Figure 1:
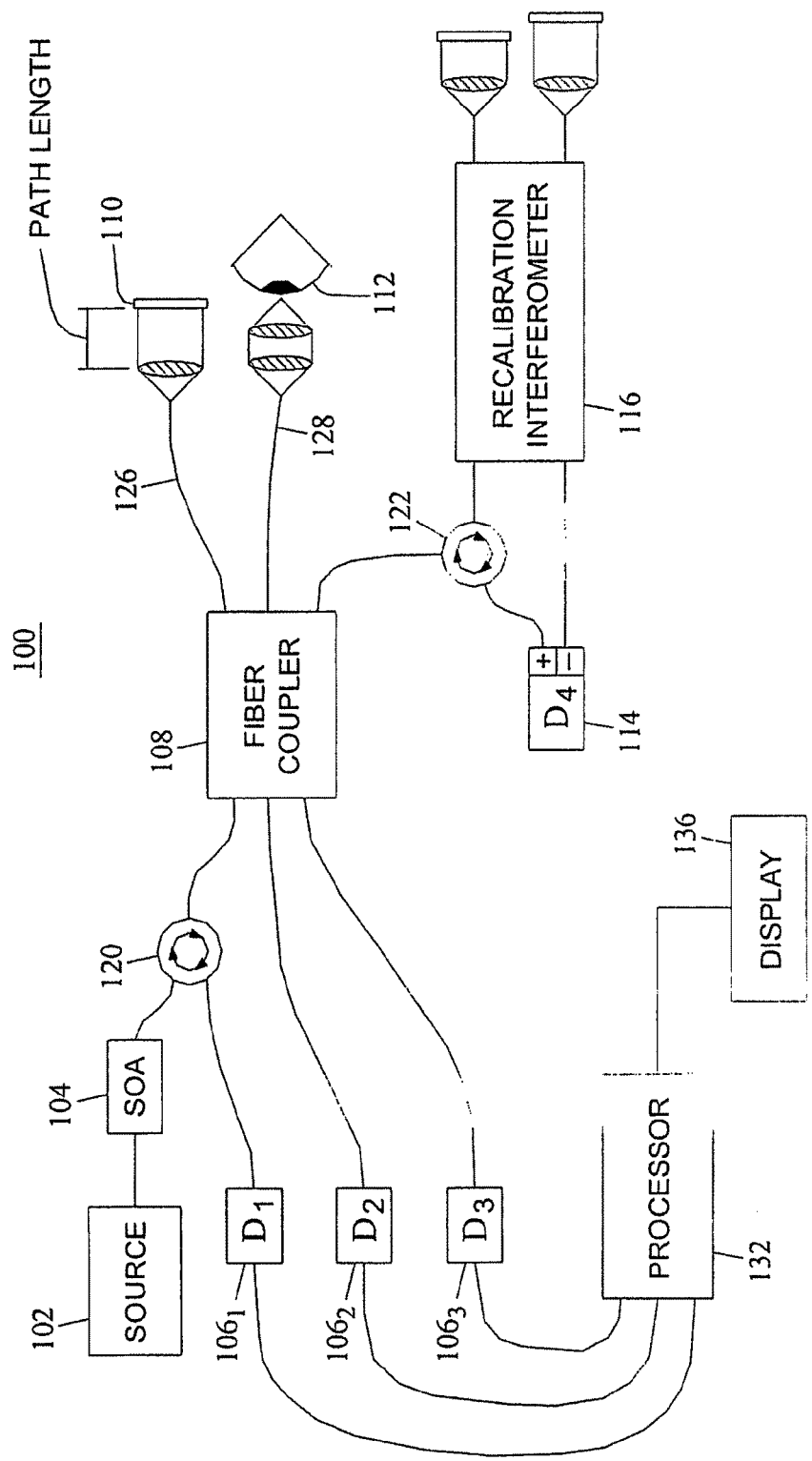
FIG. 1 is a diagram illustrating an exemplary OCT interferometry system according to an embodiment of the subject matter described herein.

FIG. 1 depicts an exemplary OCT system that may be used to implement the present subject matter. Although FIG. 1 describes the present subject matter in the context of an exemplary 3×3 swept source OCT (SS OCT) system used for high speed, real-time imaging an ocular anterior segment, the subject matter described herein may be applied generally to other OCT applications or may be implemented in any suitable interferometer device or system.

Referring to FIG. 1, OCT system 100 includes a source 102, a semiconductor optical amplifier (SOA) 104, a plurality of detectors $106_{1...3}$, a fiber coupler 108, a reflectance mirror 110, a sample 112, a $4^{th}$ detector 114, a first optical circulator 120, a second optical circulator 122, and a recalibration interferometer 116. OCT system 100 may also include a processing unit 132 and a display unit 136.

Source 102 may include any broadband short-coherence length light source (e.g., a source having multiple wavelengths or modes) or any comparable light source mechanism. In one embodiment, source 102 may be a tunable Fabry-Perot fiber ring swept laser. Alternatively, source 102 may also comprise a narrowband source if desired. Source 102 is followed by SOA 104. In one embodiment, SOA 104 may include a booster semiconductor optical amplifier. After being amplified by SOA 104, the source signal proceeds to fiber coupler 108 via optical circulator 120. Fiber coupler 108 may include a 3×3 fiber coupler or equivalent mechanism. In one embodiment, fiber coupler 108 is a fiber optic based splitter that is designed to split the source signal between three optical paths. Optical circulator 120 is a component that used to route light more efficiently from source 102 to a sample arm 128 and a reference arm 126. Optical circulator 120 aids with the routing of backscattered light from the sample back to the detector $106_1$. In an exemplary embodiment, the three optical paths from fiber coupler 108 lead to the sample arm 128, reference arm 126, and recalibration interferometer 116 via the second optical circulator 122. Similarly, fiber coupler 108 may be configured to induce a given phase shift to interferogram signals depending on the coupler's splitting ratio.

In the sample arm 128, the source signal strikes sample 112 and a small amount of light is reflected back into fiber coupler 108. In the reference arm 126, the source signal strikes a moving reference mirror 110 and a portion of the source signal light is reflected back to fiber coupler 108. The light beams reflected back from both the sample arm 128 and the reference arm 126 are then recombined in fiber coupler 108 (in either a constructive or destructive manner) depending on the path lengths of reference mirror 110 and sample 112. The interference pattern of light reflected or backscattered from sample 112 and light from reference mirror 110 contains information about the location and scattering amplitude of the scatters in sample 112.

After recombining the reflected light, fiber couple 108 splits the light signal and provides the divided light (i.e., detector signals) to detectors $106_{1...3}$. Detectors $106_{1...3}$ may include spectrometers, array detectors, or any like components that processes detector signals in order to derive a complex interferometric signal. Specifically, as reference mirror 110 modifies the path length in the reference arm, the detectors observe a series of constructive and destructive combinations of reflected light. Notably, the series of light combinations may be used to generate an interferogram. The detector signals from detectors $106_{1...3}$ are ultimately received by processing unit 132. In one embodiment, the detector signals may be filtered prior to arriving at processing unit 132. Processing unit 132 may include any processing mechanism, such as a desktop computer, a laptop computer, a personal digital assistant (PDA), and the like. Notably, processing unit 132 is responsible for performing the computations for deriving a complex interferogram signal from the filtered detector signals. Processing unit 132 then produces a signal output which is then provided to display unit 136. Display unit 136 may include any display screen, such as a computer monitor, laptop screen, television, and the like. Specifically, display unit 136 is capable of displaying a complex conjugate resolved image that is constructed from the complex inteferogram signal.

System 100 may be readily configured to display complex conjugate resolved FDOCT images. Notably, processing unit 132 may be adapted to perform a number of computation intensive tasks that are required to perform the method 200 below. In one embodiment, the processing unit 132 may execute a software program or any other computer readable medium to accomplish this goal.

Figure 2:
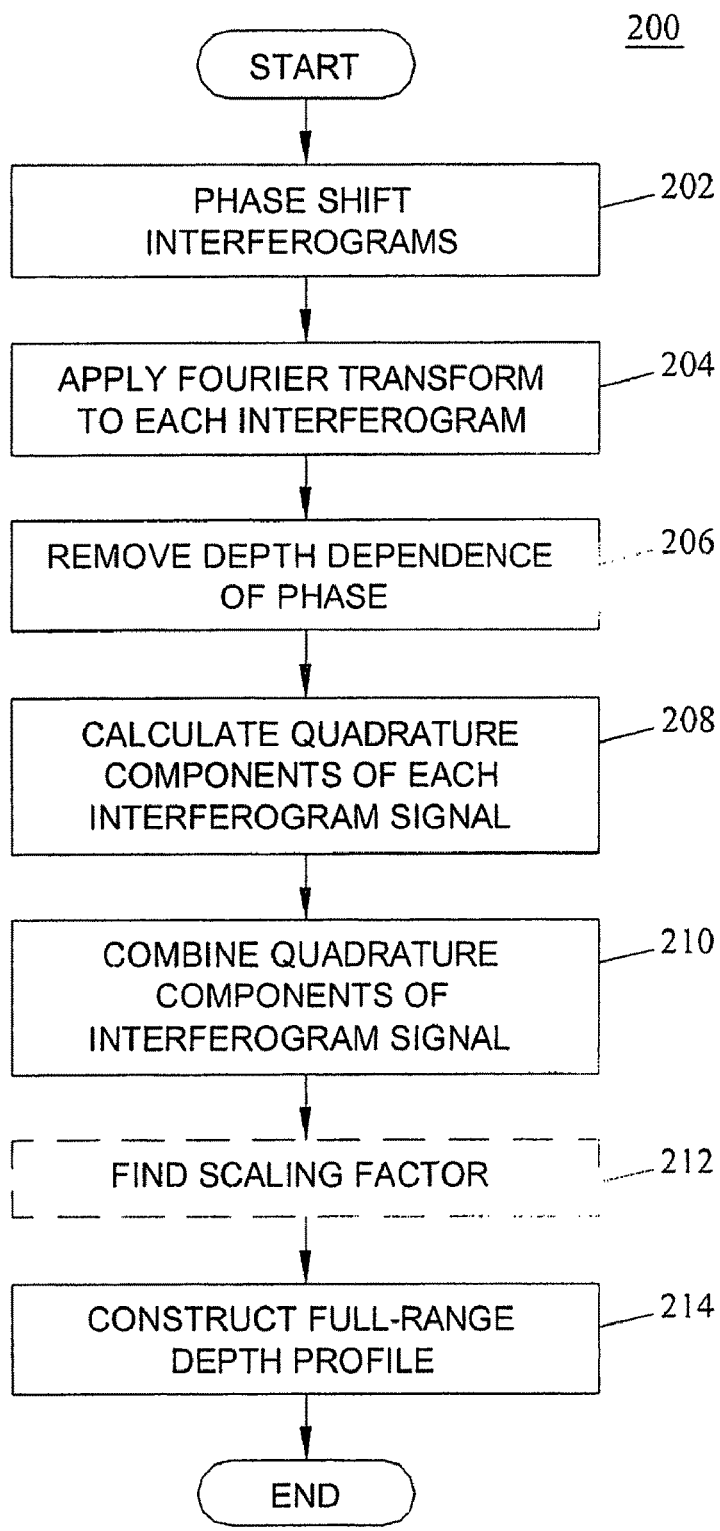
FIG. 2 is a flow chart depicting an exemplary process for performing quadrature projection processing according to an embodiment of the subject matter described herein.

FIG. 2 is a flow chart that depicts an exemplary method 200 for performing real-time, quadrature projection based Fourier domain (FD) optical coherence tomography (OCT) according to an embodiment of the subject matter described herein. Referring to FIG. 2, in block 202, each of a plurality of interferogram signals is separated by an induced phase shift. In one embodiment, an interferogram signal is derived from interferometric components of a detector signal in a phase-shifting FDOCT system. The interferogram component of the detector signal may be represented as $s_n(k) \propto \Sigma A_m \cos(2\Delta z_m k+\theta_m+\phi_n)$, where $\Delta z_m$, $A_m$ and $\theta_m$ respectively represent the axial distance, the reflectance, and relative phase of the $m^{th}$ scatterer (e.g., a light deflecting particle or pit) in the sample to be analyzed. Similarly, $\phi_n$ represents an additional phase shift introduced for the $n^{th}$ phase shifted acquisition.

Figure 3:
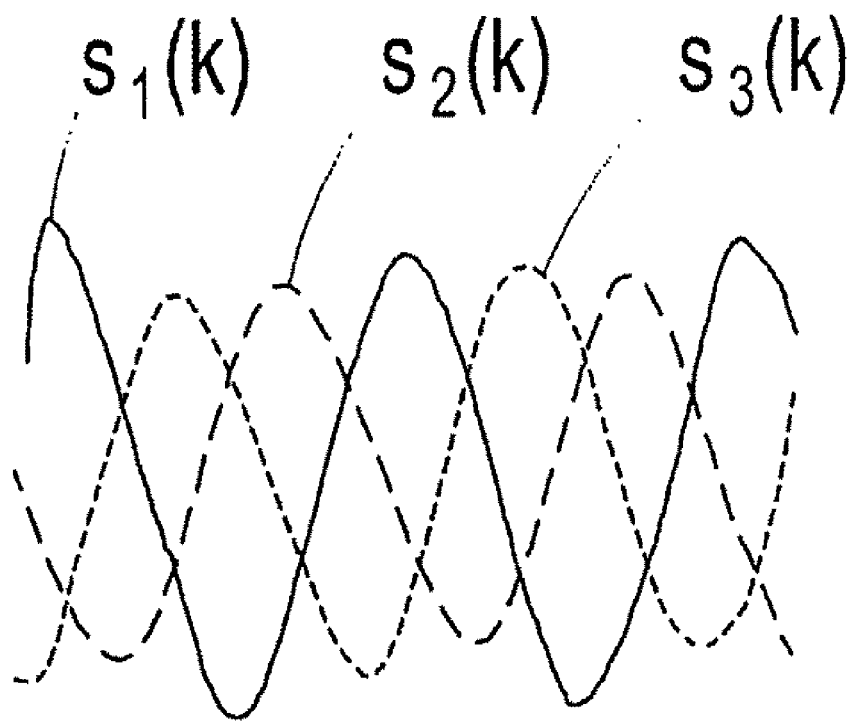
FIG. 3 is a diagram depicting phase-shifted interferogram signals according to an embodiment of the subject matter described herein.

Consider the scenario where three separate interferogram signals (or interferograms), $s_1(k)$, $s_2(k)$, and $s_3(k)$, are separated by a nominal phase shift of 120 degrees. More specifically, each interferogram signal is phase shifted by 120 degrees in relation to the previous signal. For example, $s_2(k)$ is shifted 120 degrees in relation to $s_1(k)$ and $s_3(k)$ is phase shifted 120 degrees from $s_2(k)$. FIG. 3 is an exemplary illustration of the phase-shifted interferogram signals, $s_1(k)$, $s_2(k)$, and $s_3(k)$. In one embodiment, interferogram signals are provided as output from detectors 106.

Figure 4:
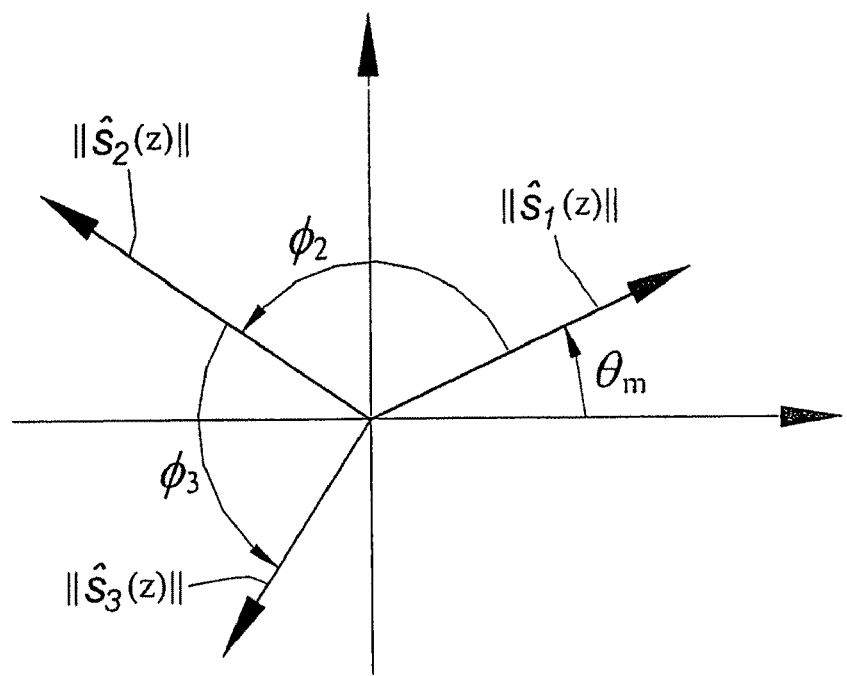
FIG. 4 is a diagram depicting Fourier transformed signals that are represented vectorally in the complex plane according to an embodiment of the subject matter described herein.

In block 204, the Fourier transform of each interferogram signal is taken. Specifically, each of the interferogram signals $s_1(k)$, $s_2(k)$, and $s_3(k)$ is subjected to a Fourier transformation operation. In one embodiment, the Fourier transform of each phase shifted interferogram signal may be a complex array whose values are the coefficients of a least squares fit of the interferogram signal by a summation of sine and cosine functions. For discretely sampled systems, a discrete Fourier Transform (DFT) or Fast Fourier Transform (FFT) (when the number of sample is a power of two) may be used. Because the interferogram signals differ only by an external phase shift (i.e., corresponding to less than a wavelength), the Fourier transform of each signal, $\hat{s}_n(z)=FT\{s_n(k)\}$, has the same intensity depth profile. However, the phase at each corresponding depth differs by the induced phase shift, $\phi_n$ as shown in FIG. 4. FIG. 4 depicts Fourier transformed phase-shifted interferogram signals in the complex plane. The Fourier transformed interferogram signals, $\hat{s}_n(z)$, may be represented vectorally in the complex plane by plotting the depth resolved magnitude $\|\hat{s}_n(z_m)\|$ at an angle $\theta_m+\phi_n$, where the possible values of $\theta_m$ range from 0 to $2\pi$. Although additional reflectors may be utilized to generate interferograms in accordance to the present subject matter, FIG. 4 only illustrates results for a single reflector for clarity purposes.

Returning to FIG. 2, in block 206, the depth dependence of the phase $\theta_m$ is removed in order to align the phase at all depths with the induced phase shift $\phi_n$. Knowledge of $\theta_m$, which fills a $2\pi$ distribution, is required to correctly sum the quadrature components of the phase shifted interferogram signals. To simplify accounting for the phase of each reflector, the phase profile of one detector signal may be artificially aligned to zero for one phase shifted signal by subtracting its phase profile from each of the phase shifted signals, thus maintaining the phase relationship induced by the fiber coupler. In one embodiment, this may be accomplished by subtracting the phase profile of the first transformed interferogram signal, which is arbitrarily selected to be aligned with the positive real axis, from each of the transformed phase shifted signals. Specifically, the expression $\hat{s}_n'(z)=\|\hat{s}_n(z)\|\exp[\arg(\hat{s}_n(z))-\arg(\hat{s}_1(z))]$ may be used. As an example, the aligning of the second transformed signal ($\hat{S}_2'(z)$) may be determined by subtracting the phase profile of the second signal from the phase profile of the first signal (i.e., $\hat{s}_2'(z)=\|\hat{s}_2(z)\|\exp[\arg(\hat{s}_2(z))-\arg(\hat{s}_1(z))]$). The result of this alignment (i.e., phase subtraction) process for a single reflector is illustrated vectorally in FIG. 5, which shows that transformed signal $\hat{s}_1'(z)$ is aligned with the positive real axis while the remaining phase shifted signals are forced onto the angle induced by the phase shift, $\phi_n$. Notably, the phase relationship between the shifted interferogram signals is maintained. This phase subtraction results in a negligible axial shift of each scatterer by up to half a wavelength (e.g., up to $\pi$), which is much smaller than the coherence length for practical light sources used in OCT. Note that the phase is referenced relative to the first transformed detector signal, and does not require knowledge of $\phi_n$.

Returning to FIG. 2, in block 208, the quadrature components of each phase referenced signal $\hat{s}_n'(z)$ are determined. As illustrated by the dashed arrows in FIG. 5, this step is analogous to calculating the projection of each vector (associated with each transformed phased shifted signal) onto the real and imaginary axes. In one embodiment, this may be performed via Fourier decomposition by simply expressing the complex valued transformed signals $\hat{s}_n'(z)$ (e.g., $\hat{s}_1'(z)$, $\hat{s}_2'(z)$, and $\hat{s}_3'(z)$) in rectangular coordinates and determining the respective real and imaginary parts, $\hat{s}_n^{RE}(z)=Re\{\hat{s}_n'(z)\}$ and $\hat{s}_n^{IM}(z)=Im\{\hat{s}_n'(z)\}$ for each interferogram.

Figure 5:
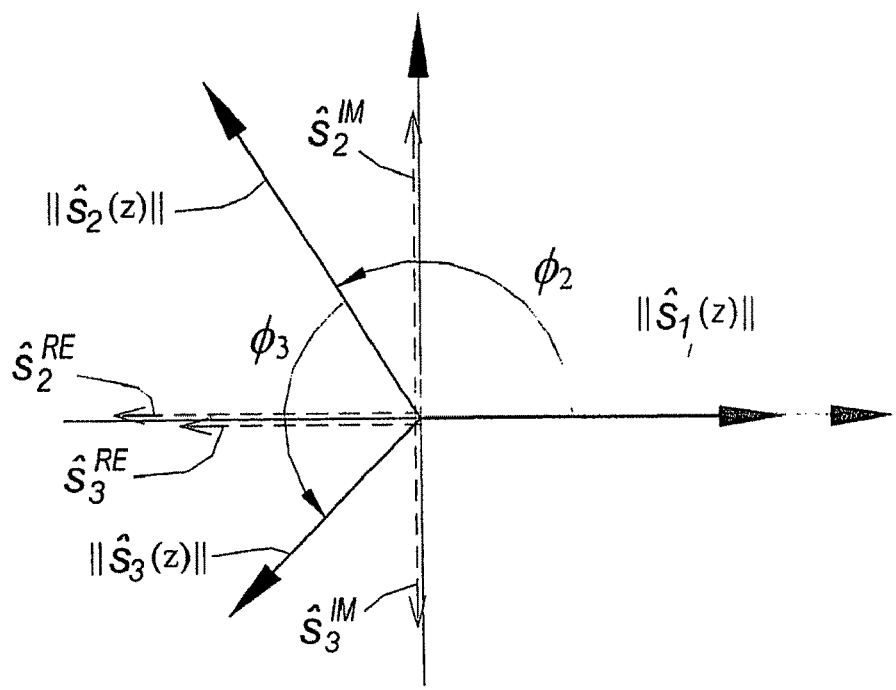
FIG. 5 is a diagram depicting the projection of vectors onto the real and imaginary axes according to an embodiment of the subject matter described herein.

Referring to FIG. 5, each of the transformed signals $\hat{s}_1(z)$, $\hat{s}_2(z)$, and $\hat{s}_3(z)$ are broken down into rectangular coordinates, or "quadrature components." For example, $\hat{s}_2(z)$ is broken down to quadrature components $\hat{s}_2^{RE}(z)$ and $\hat{s}_2^{IM}(z)$ and $\hat{s}_3(z)$ is broken down to $\hat{s}_3^{RE}(z)$ and $\hat{s}_3^{IM}(z)$. Although not explicitly depicted in FIG. 5, $\hat{s}_1(z)$ is broken down to quadrature components $\hat{s}_1^{RE}(z)$ and $\hat{s}_1^{IM}(z)$ as well, but component $\hat{s}_1^{IM}(z)$ has no value because $\hat{s}_1(z)$ lies completely on the real axis (and thus, is entirely equivalent to component $\hat{s}_1^{RE}(z)$).

Notably, the derived $\hat{s}_n^{RE}(z)$ and $\hat{s}_n^{IM}(z)$ are in quadrature irrespective of the induced phase shift $\phi_n$ because the cosine and sine basis functions are orthogonal. More specifically, this operation corresponds to Fourier decomposition of the phase-referenced signals, with the cosine and sine basis functions aligned with the positive real and imaginary axes, respectively. These decomposed signals are thus separated in phase by precisely 90 degrees, and are thus said to be in quadrature. The choice of Fourier decomposition with cosine and sine basis functions is convenient but not critical to the processing quadrature projection algorithm which is compatible with any set of orthogonal basis functions. Also, dependence of $\phi_n$ on wavenumber (i.e., inverse of wavelength) does not affect the orthogonality of the projections. Note that both $\hat{s}_n^{RE}(z)$ and $\hat{s}_n^{IM}(z)$ are real valued, and that the depth profile of $\hat{s}_n^{RE}(z)$ is symmetric about the reference position, whereas $\hat{s}_n^{IM}(z)$ is anti-symmetric.

Figure 6:
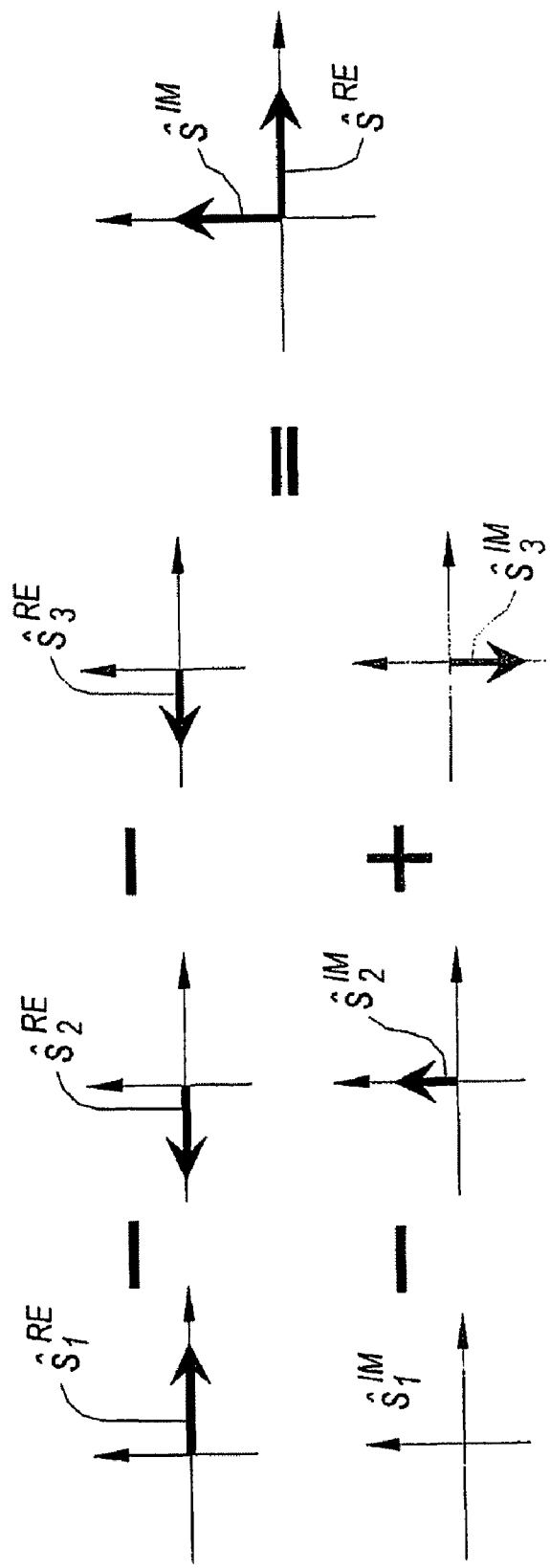
FIG. 6 is a diagram depicting the derived real and imaginary signals according to an embodiment of the subject matter described herein.

Returning to FIG. 2, in block 210, the quadrature components of the transformed phase shifted signals are combined. When utilized in conjunction with 90 degree-phase shifting techniques, only the projection along the real or imaginary axis is retained. Notably, a non-zero value of the perpendicular component represents a combination of a mis-calibrated phase shift and/or sample drift. When quadrature projection is used with non-90 degree phase shifting techniques, the real and imaginary components are of similar amplitude and both are retained. An estimate of each $\phi_n$ is required to predetermine which quadrature projected components are aligned parallel or anti-parallel to the axes, represented using $\delta_n^{RE}=\pm1$ and $\delta_n^{IM}=\pm1$. Since the sign of each $\delta_n$ is dependent only on the quadrant location of $\phi_n$, the quadrature projection algorithm is insensitive to mis-calibration or drift of the actual induced phase shift. The derived real and imaginary signals are thus determined using the relations $$\hat{s}^{RE}(z) = \sum_n \delta_n^{RE} \hat{s}_n^{RE}, \text{ and } \hat{s}^{IM}(z) = \sum_n \delta_n^{IM} \hat{s}_n^{IM},$$

as illustrated in FIG. 6.

Returning to FIG. 2, in optional block 212, the derived quadrature components $\hat{s}^{RE}(z)$ and $\hat{s}^{IM}(z)$ are scaled to account for unequal contributions to the real and imaginary quadrature components. Specifically, the derived real and imaginary signals may require scaling to normalize their respective amplitudes. A variety of techniques may be used to determine the optimal scaling factor. For example, a normalizing scalar may be obtained by taking the ration of the summed magnitude of the real and imaginary vectors. Alternatively, an iterative process, either manual or computational, may be used to determine the optimal scaling factor $\beta$ for suppression of any possible complex conjugate artifact from a strong reflector. In one embodiment, the derived quadrature components may be scaled relative to each other by calculating $\beta$ as the ratio of the maximum value of $\hat{s}^{RE}$ to $\hat{s}^{IM}$. In another embodiment, the scaling coefficient $\beta$ may represent the ratio of the total energy in the derived real signal to that of the derived imaginary signal. Specifically, $\beta$ may be represented as $\beta = \sqrt{\int |\hat{s}^{RE}(z)|^2 dz / \int |\hat{s}^{IM}(z)|^2 dz}$.

Figure 7:
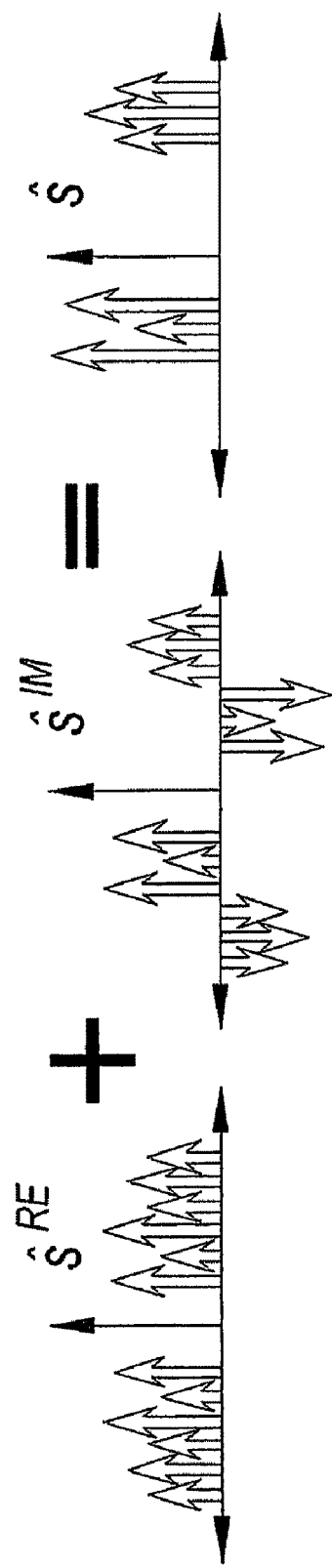
FIG. 7 is a diagram depicting the cancellation of symmetric complex conjugate artificial peaks to determine the full range depth profile according to an embodiment of the subject matter described herein.

Returning to FIG. 2, in block 214, the complex conjugate resolved image is obtained. In one embodiment, the complex conjugate resolved image (e.g., an A-scan ultrasound biometry) is obtained by directly adding the derived real component and the scaled imaginary component, i.e., $\hat{s}(z)=\hat{s}^{RE}(z)+\beta \hat{s}^{IM}(z)$. This allows for unambiguous discrimination of positive and negative distances. The summation is illustrated in FIG. 7, which shows the cancellation of the symmetric complex conjugate artifact peaks in $\hat{s}^{RE}(z)$ by the anti-symmetric peaks in $\hat{s}^{IM}(z)$, thereby resulting in the full range depth profile $\hat{s}^{RE}(z)$ (which may ultimately be used to construct a complex conjugate resolved image).

Quadrature projection processing as described herein was demonstrated using three non-90° phase shifted interferograms acquired simultaneously from the ports of the 3×3 Michelson type interferometer as illustrated in FIG. 1. The source was a tunable Fabry-Perot fiber ring swept laser (e.g., Micron Optics) followed by a booster semiconductor optical amplifier (e.g., InPhenix), providing a source bandwidth of 84 nm FWHM centered at 1310 nm, and an average power in excess of 8 mW at the sample. The source was driven with a 3.33 kHz triangular wave, providing an effective 6.67 kHz line rate by processing both forward and backward sweeps. The sample arm was mounted on a customized slit lamp with galvanometer mounted scanning mirrors. A calibration signal from a 2×2 fiber Michelson interferometer was used to re-sample the data channels using a "nearest-neighbor" algorithm. All four channels were digitized simultaneously at 10 MHz (e.g., National Instruments PCI 6115), from four photodiode detectors (e.g., New Focus; $D_{1-3}$, model 1817, and $D_4$, model 1617).

Figure 8:
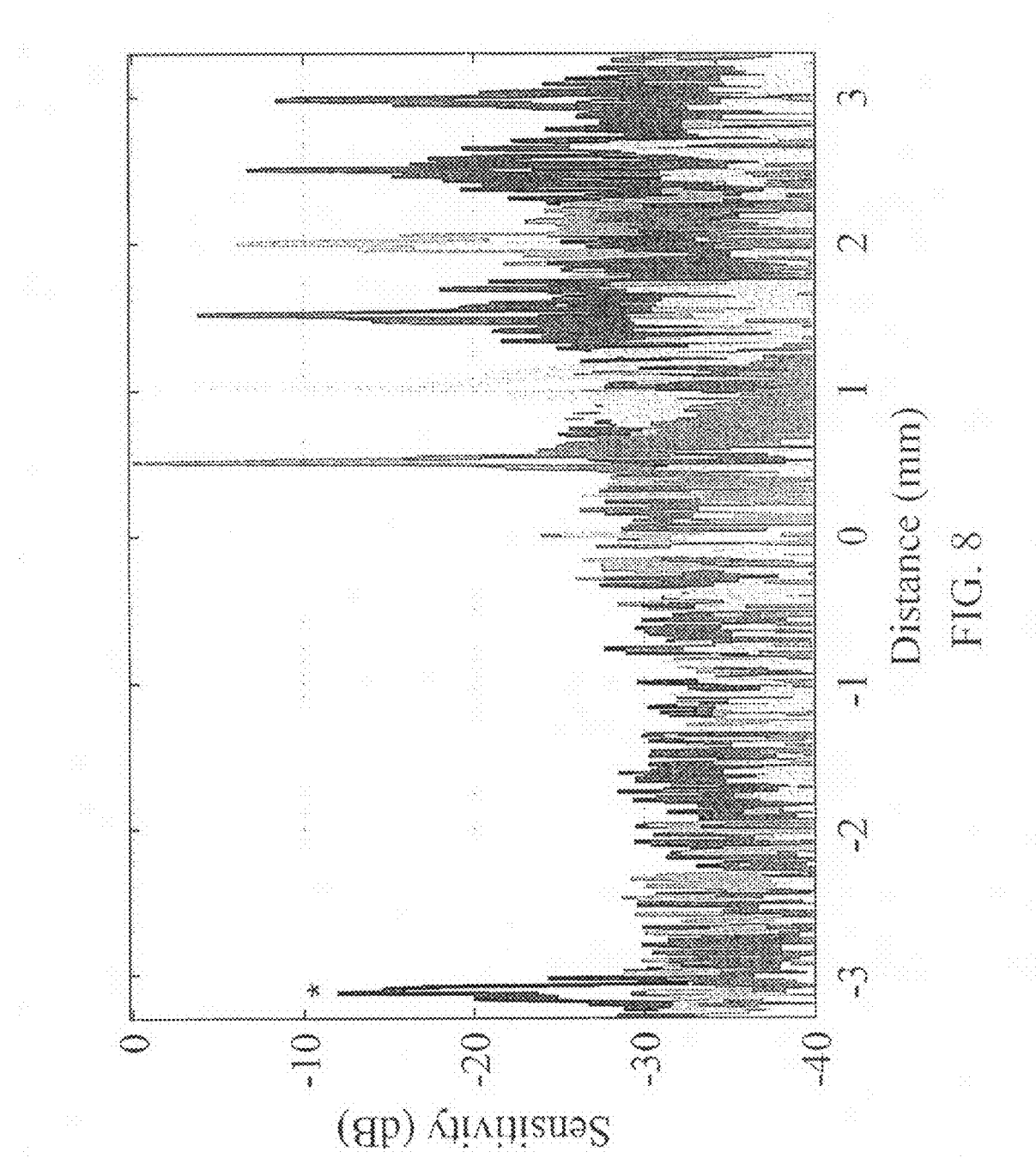
FIG. 8 is a chart depicting a complex conjugate resolved A-scan according to an embodiment of the subject matter described herein.

The optical power at the sample was reduced to 3.75 mW for ocular anterior segment imaging, and this value was used to measure the system sensitivity. The complex conjugate suppression and system sensitivity measurements are presented in FIG. 8 for a −50 dB attenuator in the sample arm. The complex conjugate resolved A-scans achieve >30 dB suppression of the symmetric artifact. The double-sided image depth was 6.6 mm, as indicated in FIG. 8. The peak system sensitivity, accounting for re-coupling losses, was measured to be 103 dB near DC and decreased by 8 dB at the ends of the depth scan.

Figure 9:
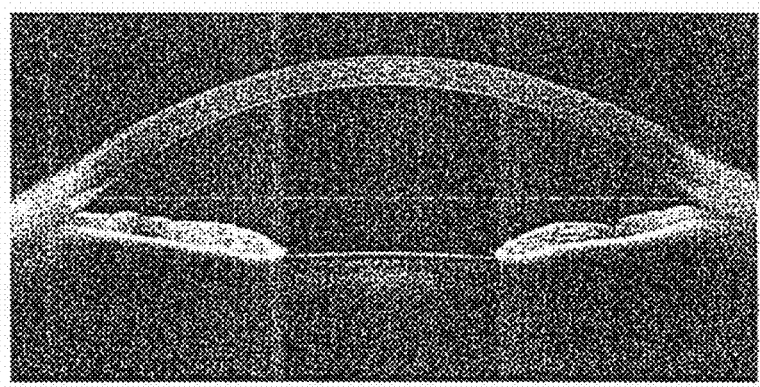
FIG. 9 is a pair of in vivo full depth images of the ocular anterior segment according to an embodiment of the subject matter described herein.
Figure 9:
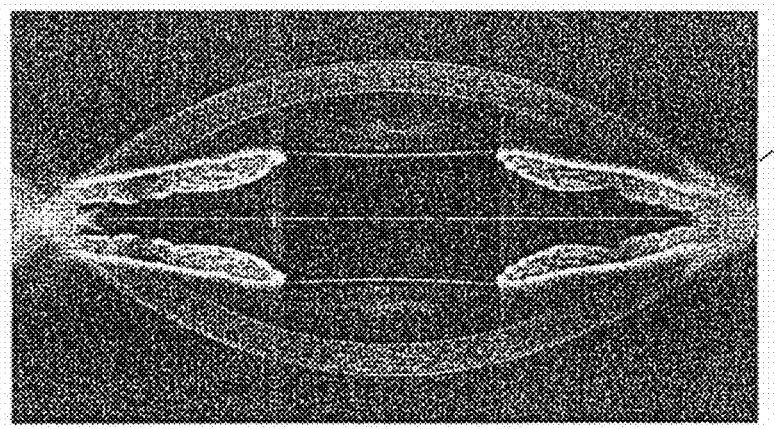

FIG. 9 depicts in vivo full depth images of the ocular anterior segment of human volunteers. The images were obtained using a combination of a 3×3 SS OCT system with quadrature projection processing. Corruption of the complex conjugate resolved image due to sample motion was not observed, since the phase-shifted interferograms from the 3×3 interferometer were acquired simultaneously. In one embodiment, the image processing may be performed by a standard desktop computer (e.g., Intel Pentium D 3.2 GHz) executing C++ programs or any other suitable program language. The nearest neighbor resampling and quadrature projection algorithm may be performed and displayed in real time on 1,024 point A-scans, for 800 lines per frame at 6.7 frames per second. In FIG. 9, a generated complex conjugate resolved image 901 is compared against an unresolved image 902 (obtained by averaging the Fourier transformed detector outputs). Notably, image 901 demonstrates a full depth, artifact free image of a human eye anterior segment acquired in vivo. Conversely, image 902 depicts the human eye anterior segment that is corrupted by the complex conjugate artifact.

In conclusion, a method for complex conjugate resolved FDOCT with arbitrarily spaced phase shifts is presented. Although the method was described for ~120 degree phase shifted interferometry using a 3×3 fiber coupler, the present subject matter is generally applicable for correction of mis-calibrated phase shifts obtained by other phase shifting techniques.

It will be understood that various details of the subject matter described herein may be changed without departing from the scope of the subject matter described herein. Furthermore, the foregoing description is for the purpose of illustration only, and not for the purpose of limitation.

What is claimed is:

1. A method for performing real-time quadrature projection processing to produce a full-range image of an object, the method comprising:
   (a) applying a Fourier transform to each individual interferogram signal of a plurality of interferogram signals, generated by projecting light from a light source onto an object of interest and detecting light reflected from the object and from at least one reference source;
   (b) calculating a real quadrature component and an imaginary quadrature component for each of the plurality of transformed interferogram signals;
   (c) combining the real quadrature components of the transformed interferogram signals to generate a derived real component and combining the imaginary quadrature components of the transformed interferogram signals to generate a derived imaginary component;
   (d) constructing a full-range depth profile of the object by combining the derived real component and the derived imaginary component; and
   (e) generating a full-range depth image of the object using the full-range depth profile.

2. The method of claim 1, wherein the plurality of interferogram signals comprises a first interferogram signal and a remaining plurality of interferogram signals, wherein each of the remaining plurality of interferogram signals is phase shifted from the first interferogram signal in accordance to an angle of an induced phase shift.

3. The method of claim 1, further comprising removing depth dependence of a relative phase associated with the plurality of transformed interferogram signals.

4. The method of claim 3, wherein the removing step includes subtracting the phase profile of a first transformed interferogram signal belonging to the plurality of transformed interferogram signals from each of the remaining plurality of transformed interferogram signals.

5. The method of claim 4, wherein the subtracting step is represented as $\hat{s}_n'(z)=\|\hat{s}_n(z)\|\exp[\arg(\hat{s}_n(z))-\arg(\hat{s}_1(z))]$ where $\hat{s}_1(z)$ is the first transformed interferogram signal and $\hat{s}_n(z)$ represents one of the remaining plurality of transformed interferogram signals.

6. The method of claim 3, wherein the removing step comprises:
   (a) aligning a vector representation of a first transformed interferogram belonging to the plurality of transformed interferogram signals onto a positive real axis; and
   (b) shifting a vector representation of each of the remaining plurality of transformed interferogram signals to an angle of an induced phase shift.

7. The method of claim 1, wherein the calculating step comprises determining a vector projection of each of the plurality of transformed interferogram signals onto a real axis and an imaginary axis.

8. The method of claim 7, wherein the determining step is performed by expressing each vector projection in rectangular coordinates and obtaining the real quadrature component and the imaginary quadrature component for each vector projection.

9. The method of claim 8, wherein the combining step comprises respectively summing the real quadrature components of the vector projections to generate the derived real component and summing the imaginary quadrature component of the vector projections to generate the derived imaginary component.

10. The method of claim 1, wherein combining the derived real component and the derived imaginary component comprises adding the derived real component to the product of the derived imaginary component and a scaling factor.

11. The method of claim 10 wherein the scaling factor comprises a ratio of the summed magnitude of the derived real component and the derived imaginary component.

12. The method of claim 10, wherein the scaling factor $\beta$ comprises a value represented as $\beta=\sqrt{\int|\hat{s}^{RE}(z)|^2 dz / \int|\hat{s}^{IM}(z)|^2 dz}$ where $|\hat{s}^{RE}(z)|^2$ is a total energy in the derived real component and $|\hat{s}^{IM}(z)|^2$ is a total energy in the derived imaginary component.

13. The method of claim 1, wherein the plurality of interferogram signals comprises interferometric components of detector signals.

14. The method of claim 1, wherein the full range depth profile is used to construct a complex conjugate resolved image.

15. The method of claim 1, wherein the Fourier transform comprises at least one of a Discrete Fourier Transform and a Fast Fourier transform.

16. The method of claim 1, wherein the Fourier transform comprises a complex array containing values that are coefficients of a least squares fit of at least one of the plurality of interferogram signals by a summation of sine and cosine functions.

17. The method of claim 1, wherein the object of interest comprises biological tissue.

18. The method of claim 17, wherein the biological tissue comprises an ocular anterior segment of a human eye.

19. A system for performing real-time quadrature projection processing to produce a full-range image of an object, the system comprising:
   (a) an interferometer for generating a plurality of interferogram signals, wherein the plurality of interferogram signals are generated by projecting light from a light source onto an object of interest and detecting light reflected from the object and from at least one reference source; and
   (b) a processing unit for applying a Fourier transform to each individual interferogram signal of the plurality of interferogram signals, calculating a real quadrature component and an imaginary quadrature component for each of the plurality of transformed interferogram signals, combining the real quadrature components of the transformed interferogram signals to generate a derived real component and combining the imaginary quadrature components of the transformed interferogram signals to generate a derived imaginary component, constructing a full-range depth profile of the object by combining the derived real component and the derived imaginary component;
   and generating a full-range depth image of the object using the full-range depth profile.

20. The system of claim 19, wherein the plurality of interferogram signals comprises a first interferogram signal and a remaining plurality of interferogram signals, wherein each of the remaining plurality of interferogram signals is phase shifted from the first interferogram signal in accordance to an angle of an induced phase shift.

21. The system of claim 19, wherein the processing unit is further adapted to subtract the phase profile of a first transformed interferogram signal belonging to the plurality of transformed interferogram signals from each of the remaining plurality of transformed interferogram signals.

22. The system of claim 21, wherein the subtraction of the phase profile is represented as $\hat{s}_n'(z)=\|\hat{s}_n(z)\|\exp[\arg(\hat{s}_n(z))-\arg(\hat{s}_1(z))]$ where $\hat{s}_1(z)$ is the first transformed interferogram signal and $\hat{s}_n(z)$ represents one of the remaining plurality of transformed interferogram signals.

23. The system of claim 19, wherein the processing unit is further adapted to
   (a) align a vector representation of a first transformed interferogram belonging to the plurality of transformed interferogram signals onto a positive real axis; and
   (b) shift a vector representation of each of the remaining plurality of transformed interferogram signals to an angle of an induced phase shift.

24. The system of claim 19, wherein the processing unit is further adapted to determine a vector projection of each of the plurality of transformed interferogram signals onto a real axis and an imaginary axis.

25. The system of claim 24, wherein the processing unit is further adapted to express each vector projection in rectangular coordinates and obtain the real quadrature component and the imaginary quadrature component for each vector projection.

26. The system of claim 25, wherein the processing unit is further adapted to respectively sum the real quadrature components of the vector projections to generate the derived real component and sum the imaginary quadrature component of the vector projections to generate the derived imaginary component.

27. The system of claim 19, wherein the processing unit is configured for combining the derived real component and the derived imaginary component by adding the derived real component to the product of the derived imaginary component and a scaling factor.

28. The system of claim 27 wherein the scaling factor comprises a ratio of the summed magnitude of the derived real component and the derived imaginary component.

29. The system of claim 27, wherein the scaling factor β comprises a value represented as $\beta = \sqrt{\int |\hat{s}^{RE}(z)|^2 dz / \int |\hat{s}^{IM}(z)|^2 dz}$ where $|\hat{s}^{RE}(z)|^2$ is a total energy in the derived real component and $|\hat{s}^{IM}(z)|^2$ is a total energy in the derived imaginary component.

30. The system of claim 19, wherein the plurality of interferogram signals comprises interferometric components of detector signals.

31. The system of claim 19, wherein the full range depth profile is used to construct a complex conjugate resolved image.

32. The system of claim 19, wherein the Fourier transform comprises at least one of a Discrete Fourier Transform and a Fast Fourier transform.

33. The system of claim 19, wherein the Fourier transform comprises a complex array containing values that are coefficients of a least squares fit of at least one of the plurality of interferogram signals by a summation of sine and cosine functions.

34. The system of claim 19, wherein the object of interest comprises biological tissue.

35. The system of claim 34, wherein the biological tissue comprises an ocular anterior segment of a human eye.

36. The system of claim 19, wherein the processing unit is configured to remove depth dependence of a relative phase associated with the plurality of transformed interferogram signals.

37. A computer program product comprising computer executable instructions embodied in a non-transitory computer readable medium for performing steps comprising:
(a) applying a Fourier transform to each individual interferogram signal of a plurality of interferogram signals, generated by projecting light from a light source onto an object of interest and detecting light reflected from the object and from at least one reference source;
(b) calculating a real quadrature component and an imaginary quadrature component for each of the plurality of transformed interferogram signals;
(c) combining the real quadrature components of the transformed interferogram signals to generate a derived real component and combining the imaginary quadrature components of the transformed interferogram signals to generate a derived imaginary component;
(d) constructing a full-range depth profile of the object by combining the derived real component and the derived imaginary component; and
(e) generating a full-range depth image of the object using the full-range depth profile.

38. The computer program product according to claim 37, wherein the steps further comprise removing depth dependence of a relative phase associated with the plurality of transformed interferogram signals.

39. The computer program product of claim 37, wherein combining the derived real component and the derived imaginary component comprises adding the derived real component to the product of the derived imaginary component and a scaling factor.

* * * * *